US005833970A

United States Patent [19]
Cox

[11] Patent Number: 5,833,970
[45] Date of Patent: Nov. 10, 1998

[54] DEODORANT MATERIAL AND DEODORIZING METHOD

[76] Inventor: James P. Cox, 246 E. Bartlett Rd., Lynden, Wash. 98264

[21] Appl. No.: 892,606

[22] Filed: May 29, 1992

Related U.S. Application Data

[63] Continuation of Ser. No. 726,144, Jun. 24, 1991, abandoned, which is a continuation of Ser. No. 530,494, May 29, 1990, abandoned, which is a continuation of Ser. No. 287,689, Dec. 20, 1988, abandoned, which is a continuation of Ser. No. 969,163, Dec. 13, 1978, abandoned, which is a continuation-in-part of Ser. No. 761,689, Jan. 24, 1977, abandoned, said Ser. No. 969,163, is a continuation-in-part of Ser. No. 932,537, Aug. 10, 1978, abandoned, which is a continuation-in-part of Ser. No. 761,689.

[51] Int. Cl.$^6$ ...................................................... A61L 9/01
[52] U.S. Cl. ........................ 424/76.1; 424/76.2; 424/76.3; 424/76.5; 424/76.6
[58] Field of Search ................................... 424/76.1, 76.3, 424/76.9, 76.5, 76.6, 76.2, 79.9

[56] References Cited

U.S. PATENT DOCUMENTS

| | | | |
|---|---|---|---|
| 1,346,337 | 7/1920 | Rourk | 424/76.1 |
| 2,314,125 | 3/1943 | Coca | 424/76.1 |
| 2,317,908 | 4/1943 | Grady | 424/76.1 |
| 2,856,330 | 10/1958 | Vagenias | 424/76.1 |
| 3,074,891 | 1/1963 | Kulka | 424/76.1 |
| 3,124,460 | 3/1964 | Erwin | 99/1 |
| 3,255,082 | 6/1966 | Barton | 424/76.1 |
| 3,509,254 | 4/1970 | Krotinger, Jr. et al. | 424/76.1 |
| 3,650,968 | 3/1972 | Hoffman | 424/76.1 |
| 3,677,405 | 7/1972 | Keith | 210/181 |
| 3,898,324 | 8/1975 | Komakine | 424/76.1 |
| 3,943,243 | 3/1976 | Kook | 424/76.1 |
| 3,989,498 | 11/1976 | Cox | 424/76.1 |
| 4,007,262 | 2/1977 | Bowers | 424/76.1 |
| 4,034,078 | 7/1977 | Van Horn | 424/76.1 |
| 4,090,470 | 5/1978 | Williams | 119/160 |
| 4,172,123 | 10/1979 | Lowicki | 424/76.1 |
| 4,229,410 | 10/1980 | Kosti | 424/76.1 |

FOREIGN PATENT DOCUMENTS

| | | | |
|---|---|---|---|
| 487338 | 3/1873 | Japan | 424/76 |
| 2057 | 5/1878 | United Kingdom | 424/76 |

*Primary Examiner*—Raj Bawa
*Attorney, Agent, or Firm*—Robert W. Beach

[57] ABSTRACT

Malodorous substances resulting from the decomposition of organic products derived from living organisms, such as acrolein, ammonia, aldehydes, cadaverine, indole, alkaloids including primary and/or secondary amines, butyric acid and skatole, separately or in combination, which may be included in polluted air escaping from rendering plants or cooks, poultry and seafood processing plants, food canneries, tanneries, sewage treatment plants or excrement receptacles, or which may be carried by or impregnated in fabrics, can be rendered unobjectionable by treatment of such air, facilities or products with metallic material including inorganic metal salts such as chlorides, sulfates, nitrates and phosphates, oxides and hydroxides. Suitable metals include aluminum, copper, iron, nickel and zinc. Usually the metallic material is carried by or contained in a liquid vehicle, but in some instances may be used in powder form. Also, in some instances, it is desirable for the liquid vehicle to be nonneutral, having a pH of 7 plus or minus at least 2, and preferably alkaline having a pH of at least 11.

1 Claim, No Drawings

DEODORANT MATERIAL AND DEODORIZING METHOD

RELATIONSHIP

This is a continuation of application Ser. No. 07/726,144 filed on Jun. 24, 1991, now abandoned, which is a continuation of application Ser. No. 07/530,494, filed May 29, 1990, now abandoned, for Deodorant Material and Deodorizing Method, which application is a continuation of U.S. patent application Ser. No. 07/287,689, filed Dec. 20, 1988, now abandoned, which application is a continuation of U.S. patent application Ser. No. 05/969,163, filed Dec. 13, 1978, now abandoned, which application is a continuation-in-part of U.S. patent application Ser. No. 05/761,689, filed Jan. 24, 1977, now abandoned, and which application Ser. No. 05/969,163 is also a continuation-in-part of U.S. patent application Ser. No. 05/932,537, filed Aug. 10, 1978, now abandoned, and which application Ser. No. 05/932,537 is also a continuation-in-part of said application Ser. No. 761,689 now abandoned.

BACKGROUND OF THE INVENTION

1. Field of the Invention

The present invention relates to material containing metallic compound for treating malodorous substances.

2. Prior Art

Van Horn U.S. Pat. No. 4,034,078, issued Jul. 5, 1977, states that a ferrous salt and proteolytic enzyme composition can be used to reduce unpleasant odors emanating from animal waste by spreading or scattering a dry powder of the material on such waste. The ferrous salt may be, for example, a sulfate, nitrate, chloride, acetate, lactate, or citrate or a mixture of various salts. Particularly such treatment is recommended to reduce the ammonia concentration. Also, this patent states that other metallic salts including cupric, zinc, manganese, ferric and aluminum salts, have known deodorant properties. The patent does not explain how or where such salts have been used for deodorant purposes.

Erwin U.S. Pat. No. 3,124,460, issued Mar. 10, 1964, states that many unpleasant odors may be eliminated or reduced by the addition to the odoriferous material of a composition comprising water-soluble ferrous and cupric compounds. Reference is made to the use of cupric copper and ferrous iron salts, preferably together, in the form of sulfates, chlorides and acetates, as well as nonionizable water-soluble copper and ferrous iron complexes in the form of gluconates, citrates, tartrates, the salts of ethylene diamine tetra acetic acid, and the sodium or potassium, iron and copper chlorophyllins. Such a deodorant composition was used on partially dried sewage sludge. Emphasis was placed on the desirability of combining ferrous iron and cupric copper compositions in both ionizable and nonionizable form. The combination of water-soluble ferrous and cupric compounds was also stated to eliminate, reduce or prevent the formation of various body odors in mammals such as humans and dogs. Such body odors were stated to include skin and hair odors, and breath odors resulting from materials adhering to the teeth, tongue and gums, i.e. mouth odors, as well as odors released in the lungs caused by ingestion of odoriferous materials such as onions and garlic.

Aluminum chlorohydrate has been used for an underarm antiperspirant. Iron sulfate has been poured into sewage lagoons for odor control purposes. These preparations have been approximately neutral instead of being strongly acidic or strongly alkaline.

SUMMARY OF THE INVENTION

It is the principal object of the present invention to utilize metallic compounds, particularly inorganic salts, in preparations for deodorizing various biological substances and particularly those of zoological origin.

More specifically it is an object to provide compositions that will deodorize fabric, such as clothing and carpets, and odors of zoological offal and excrement.

For various specific deodorizing uses, it is a further object to combine a metal inorganic salt or metal salts with other ingredients to increase the effectiveness of the total composition or to facilitate its utilization for deodorizing purposes. For some applications, inclusion of an alkalizing agent or an acidifying agent to make the deodorizing material nonneutral greatly increases the deodorizing effectiveness of the composition.

DETAILED DESCRIPTION

Malodorous substances resulting from the decomposition of organic products derived from living organisms, such as acrolein, ammonia, aldehydes, cadaverine, indole, alkaloids, including primary and/or secondary amines, butyric acid and skatole, separately or in combination, which may be included in polluted air escaping from rendering plants or cooks, poultry and seafood processing plants, food canneries, tanneries, sewage treatment plants or excrement receptacles, or which may be carried by or impregnated in fabrics, can be rendered unobjectionable by treatment of such air, facilities or products with the deodorant composition of the present invention.

The deodorant composition of the present invention can include one or more compounds, particularaly inorganic salts, such as chlorides, sulphates, nitrates, phosphates, oxides and hydroxides of one or more of the metals aluminum, iron, copper, potassium and zinc. An inorganic salt or salts of nickel can also be used for materials being treated which do not come into contact with the human body, either internally for food purposes or externally, such as clothing.

For some deodorizing purposes, it is desirable for the deodorizing composition to be nonneutral, either acid or alkaline, having a pH range of 7 minus or plus 2, i.e. less than 5 or more than 9. For some purposes the metallic material should be strongly alkaline having a pH of 11 or more. For treating a gas stream, the metallic content can actually be dissolved or suspended in a liquid vehicle which is sprayed into the gas stream.

A preferred type of metal is aluminum provided in the form of a soluble inorganic salt. Aluminum material has been found to have good general deodorizing properties. Such salt can be utilized in powder form for some purposes and for other purposes can be dissolved in a liquid vehicle which preferably is of acidic or alkaline character within the pH range stated above, namely, below a pH of 5 or above a pH of 9. The vehicle can, for example, be a potassium hydroxide or a sodium hydroxide solution having a ph within the range of 11 to 14.

One example of a specific product that can be used for deodorizing fabrics carrying zoological odorants such as clothing or carpets includes the following general formula:

| Ingredient | Weight |
| --- | --- |
| inorganic metallic salt | 1% to 98% |
| soap, glycols or glycerol | 1% to 80% |
| TOTAL | 100% |

The salt can be of any one or more of the metals aluminum, ferrous iron, copper, zinc or potassium. The salt can be formed with any inorganic acid but sulfuric acid is preferred. The soap, glycols or glycerol are wetting agents and aid penetration of the deodorant product and to increase contact and may be designated generally as penetrants. The material should be in dry powder form.

A representative formula could include the following ingredients with the ranges specified:

| Ingredient | Weight |
| --- | --- |
| aluminum sulfate ($AlSO_4$) | 5% to 90% |
| ferrous sulfate ($FeSO_4$) | 1% to 90% |
| copper sulfate ($CuSO_4$) | 1% to 30% |
| soap | 3% to 60% |
| alkali (sodium or potassium hydroxide) (NaOH or KOH) | 0.01% to 10% |
| OPTIONAL INGREDIENT | |
| ethyl alcohol ($C_2H_8O$) OR isopropyl alcohol ($C_3H_8O$) | 0% to 10% |
| lemon oil | 0% to trace |
| propylene glycol ($C_3H_8O_2$) | 0% to 10% |
| TOTAL | 100% |

If desired, the soap can be replaced partly or entirely by fatty acid glycerides or by glycerol or by glycols, such as propylene glycol or triethylene glycol. The lemon oil is merely a product characterizing agent.

For use during the wash cycle in a household or commercial laundry to deodorize clothes and bedding, for example, the product may be provided in the form of cakes. A preferred formula for such cakes is as follows:

| Ingredient | Weight |
| --- | --- |
| aluminum sulfate ($AlSO_4$) | 35% |
| copper sulfate ($CuSO_4$) | 10% |
| ferrous sulfate ($FeSO_4$) | 25% |
| soap flakes | 25% |
| sodium hydroxide (NaOH) | 5% |
| lemon oil | trace |
| TOTAL | 100% |

Alternatively, such a fabric-deodorizing product can be provided in the form of a powder. Such powder is particularly useful for deodorizing carpets or rugs contaminated with mildew, pet odors or odors from substances that have been spilled on the carpet. A preferred specific carpet-cleaning formula is as follows:

| Ingredient | Weight |
| --- | --- |
| aluminum sulfate ($AlSO_4$) | 40% |
| ferrous sulfate ($FeSO_4$) | 40% |
| copper sulfate ($CuSO_4$) | 0.05% |
| soap flakes | 19% |
| sodium hydroxide (NaOH) | 0.05% |
| TOTAL | 100% |

The powder can be scattered onto the surface of a rug or carpet, allowed to stand for approximately 24 hours and then removed by vacuum. The powder could be sprinkled onto upholstery, left for a similar period of time and then removed by a vacuum. Such deodorant material can also be used to deodorize chemical toilets and animal and bird cages and litter.

Deodorizing material particularly suitable for deodorizing zoological offal has the general formula as follows:

| Ingredient | Weight |
| --- | --- |
| inorganic metal salt | 20% to 98% |
| nontoxic organic acid including citric acid ($C_6H_8O_7$) | 2% to 80% |

Optional added ingredients may be,

| Ingredient | Weight |
| --- | --- |
| organic acid, e.g. glacial acetic acids ($C_2H_4O_2$ [10% preferred] | 0% to 50% |
| primary, secondary or aromatic | 0% to 25% |
| alcohol, for example, isopropyl alcohol ($C_3H_8O$) [2% preferred] | |
| TOTAL | 100% |

The alcohol increases penetration of the deodorizing material. The citric acid acts to neutralize ammonia or ammonia-containing material and also forms salts with metals in the offal to prevent such metals acting as catalysts to promote rancidity.

It is preferred that the material include several metals within the ranges stated below.

| Ingredient | Weight |
| --- | --- |
| aluminum salt | 1% to 90% |
| iron salt | 0% to 95% |
| copper salt | 0% to 95% |

A preferred formula would be:

| Ingredient | Weight |
| --- | --- |
| aluminum sulfate ($AlSO_4$) | 39% |
| ferrous sulfate ($FeSO_4$) | 35% |
| copper sulfate ($CuSO_4$) | 35% |
| citric acid ($C_6H_8O_7$) | 26% |
| TOTAL | 100% |

Such a deodorant product can be supplied as a powder which is scattered on offal just prior to it being placed in a cooker. The amount of deodorant should be from one-quarter of a pound to one-half a pound for a five ton cook. Such deodorant is particularly effective to reduce the ammonia odor.

For treating excrement such as in sewage disposal plants, sewer lines, sumps and lagoons, deodorant of the following general formula can be used:

| Ingredient | Weight |
|---|---|
| inorganic metal salt | 10% to 90% |
| inorganic alkali metal salt, e.g. sodium or potassium metaphosphate or other phosphate or carbonate | 1% to 60% |
| paradichlorobenzene | 0% to 35% |
| TOTAL | 100% |

The phosphate or carbonate provides pH adjustment and increases the action of the metal salt on the excrement.

While the preferred metal salt is ferrous salt, salts of other metals can be used in addition to the ferrous salt within the following ranges.

| Ingredient | Weight |
|---|---|
| ferrous salt | 10% to 90% |
| aluminum salt | 0% to 90% |
| copper salt | 0% to 90% |

The preferred formula is:

| Ingredient | Weight |
|---|---|
| ferrous sulfate ($FeSO_4$) | 50% |
| sodium metaphosphate ($NaHPO_3$) | 25% |
| paradichlorobenzene ($C_6H_4Cl_2$) | 25% |
| TOTAL | 100% |

This deodorant material can be supplied as a powder metered into sewer lines, sumps, treatment tanks and lagoons. The amount supplied may be one-quarter of a pound to one pound per hour for treating solid excrement content at the rate of 20 to 50 parts of deodorant per million parts of excrement. This material not only deodorizes but also degreases sewage. The paradichloro-benzene has a degreasing action and insectistatic or insecticidal and bacteriostatic or bacteriocidal properties.

The foregoing examples illustrate that the deodorant of the present invention is devoid of and does not rely on any of enzymes, esters, formaldehyde and potassium permanganate for deodorizing.

Also the foregoing discussion and examples specified illustrate that the deodorant is not for personal body use but is used to deodorize odors of biological or zoological origin, such as sewage, excrement or offal, in fabric, clothing, carpets, upholstery, gas streams, animal or bird cages, litter, offal cooks, sewage disposal plants, sewer lines and swamps and lagoons, all of which uses are distinguished from body deodorants.

I claim:

1. Deodorant for remedially abating odors of odorant, other than for deodorizing human body odorant, the only deodorizing substance of which deodorant consists of the following ingredients:

| Ingredient | Weight |
|---|---|
| aluminum water-soluble inorganic salt | 5% to 90% |
| additional water-soluble inorganic salt of metal selected from the group consisting of iron, copper, zinc and nickel but less than the amount of aluminum water-soluble inorganic salt | at least 2% |
| glycol | 3% to 60% | and having a pH less than 5 or greater than 9 in the presence of water.

* * * * *